(12) United States Patent
Brugger et al.

(10) Patent No.: US 12,415,023 B2
(45) Date of Patent: Sep. 16, 2025

(54) DISPOSABLE MEDICAL FLOW-REGULATING DEVICE AND SYSTEM

(71) Applicant: NxStage Medical, Inc., Lawrence, MA (US)

(72) Inventors: James M. Brugger, Newburyport, MA (US); William J. Schnell, Libertyville, IL (US)

(73) Assignee: NxStage Medical, Inc., Lawrence, MA (US)

( * ) Notice: Subject to any disclaimer, the term of this patent is extended or adjusted under 35 U.S.C. 154(b) by 994 days.

(21) Appl. No.: 17/600,467

(22) PCT Filed: Apr. 8, 2020

(86) PCT No.: PCT/US2020/027246
§ 371 (c)(1),
(2) Date: Sep. 30, 2021

(87) PCT Pub. No.: WO2020/210343
PCT Pub. Date: Oct. 15, 2020

(65) Prior Publication Data
US 2022/0176027 A1 Jun. 9, 2022

Related U.S. Application Data

(60) Provisional application No. 62/831,310, filed on Apr. 9, 2019.

(51) Int. Cl.
*A61M 1/28* (2006.01)
*A61M 1/14* (2006.01)
(Continued)

(52) U.S. Cl.
CPC .............. *A61M 1/28* (2013.01); *A61M 1/155* (2022.05); *A61M 1/1565* (2022.05);
(Continued)

(58) Field of Classification Search
CPC ...... A61M 1/28; A61M 1/155; A61M 1/1565; A61M 1/159; A61M 1/152; A61M 1/156;
(Continued)

(56) References Cited

U.S. PATENT DOCUMENTS 3,957,082 A * 5/1976 Fuson ................. A61M 39/223
604/80
4,604,093 A * 8/1986 Brown .............. A61M 5/16827
137/625.11
(Continued)

FOREIGN PATENT DOCUMENTS

WO 2010039662 A2 4/2010

OTHER PUBLICATIONS

International Search Report and Written Opinion mailed Aug. 31, 2020 for International Patent Application No. PCT/US2020/027246.

(Continued)

*Primary Examiner* — James D Ponton
*Assistant Examiner* — John A Doubrava
(74) *Attorney, Agent, or Firm* — Potomac Law Group, PLLC

(57) ABSTRACT

A disposable medical flow-regulating assembly includes flow-directing units, with multiple fluid-flow lines entering each of the flow-directing units. The flow-directing units are interconnected by a fluid-flow line that extends between them. Each of the flow-directing units includes a rotational insert member that regulates which of multiple flow passages through the flow-directing unit is open and which are closed, based on the angular position of the insert member.

7 Claims, 3 Drawing Sheets

(51) Int. Cl.
*A61M 39/22* (2006.01)
*F04B 7/00* (2006.01)
*F04B 43/00* (2006.01)
*F04B 43/12* (2006.01)
*F16K 11/085* (2006.01)
*F16K 37/00* (2006.01)

(52) U.S. Cl.
CPC .......... *A61M 1/159* (2022.05); *A61M 39/223* (2013.01); *F04B 7/0046* (2013.01); *F04B 43/0081* (2013.01); *F04B 43/1238* (2013.01); *F16K 11/0853* (2013.01); *F16K 37/0041* (2013.01); *A61M 1/152* (2022.05); *A61M 1/156* (2022.05); *A61M 2039/224* (2013.01); *A61M 2205/128* (2013.01); *F04B 2201/06* (2013.01)

(58) Field of Classification Search
CPC .......... A61M 39/223; A61M 2039/224; A61M 2205/128; F04B 7/0046; F04B 43/0081; F04B 2201/06; F04B 43/12; F16K 11/0853; F16K 37/0041
See application file for complete search history.

(56) References Cited

U.S. PATENT DOCUMENTS

| | | | |
|---|---|---|---|
| 5,540,668 A * | 7/1996 | Wilson, Jr. .......... | A61M 39/223 604/80 |
| 8,292,594 B2 | 10/2012 | Tracey et al. | |
| 9,861,733 B2 | 1/2018 | Burbank et al. | |
| 9,920,846 B2 | 3/2018 | Demitroff et al. | |
| 2003/0199803 A1 | 10/2003 | Robinson et al. | |
| 2006/0118066 A1 | 6/2006 | Martins | |
| 2014/0018727 A1* | 1/2014 | Burbank .............. | A61M 1/1674 604/28 |
| 2014/0076058 A1 | 3/2014 | Brugger et al. | |
| 2014/0112828 A1* | 4/2014 | Grant ................. | A61M 1/3672 210/232 |
| 2014/0291565 A1 | 10/2014 | Maierhofer et al. | |
| 2017/0130849 A1* | 5/2017 | Demitroff ............... | F16K 11/07 |
| 2017/0296744 A1 | 10/2017 | Capone et al. | |
| 2017/0319765 A1 | 11/2017 | Wilt et al. | |

OTHER PUBLICATIONS

Invitation to Pay Additional Fees dated Jun. 17, 2020 for International Patent Application No. PCT/US2020/027246.

Extended European Search Report dated Nov. 4, 2022 for European Patent Application No. 20786875.3.

* cited by examiner

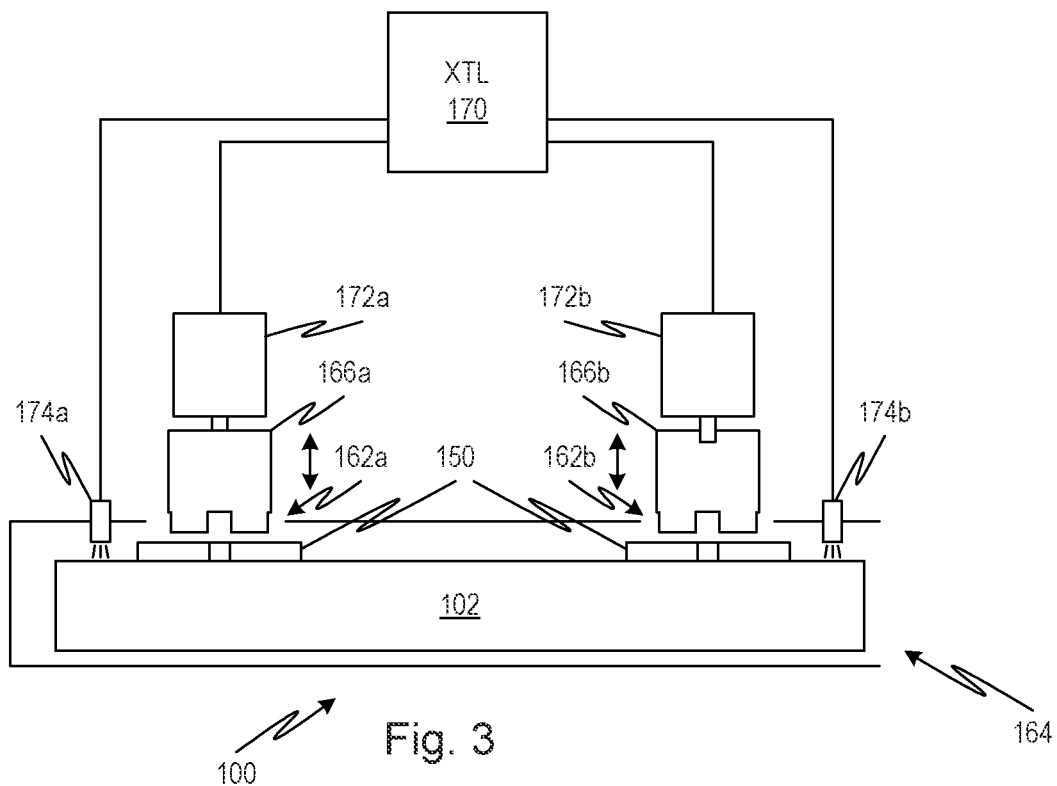
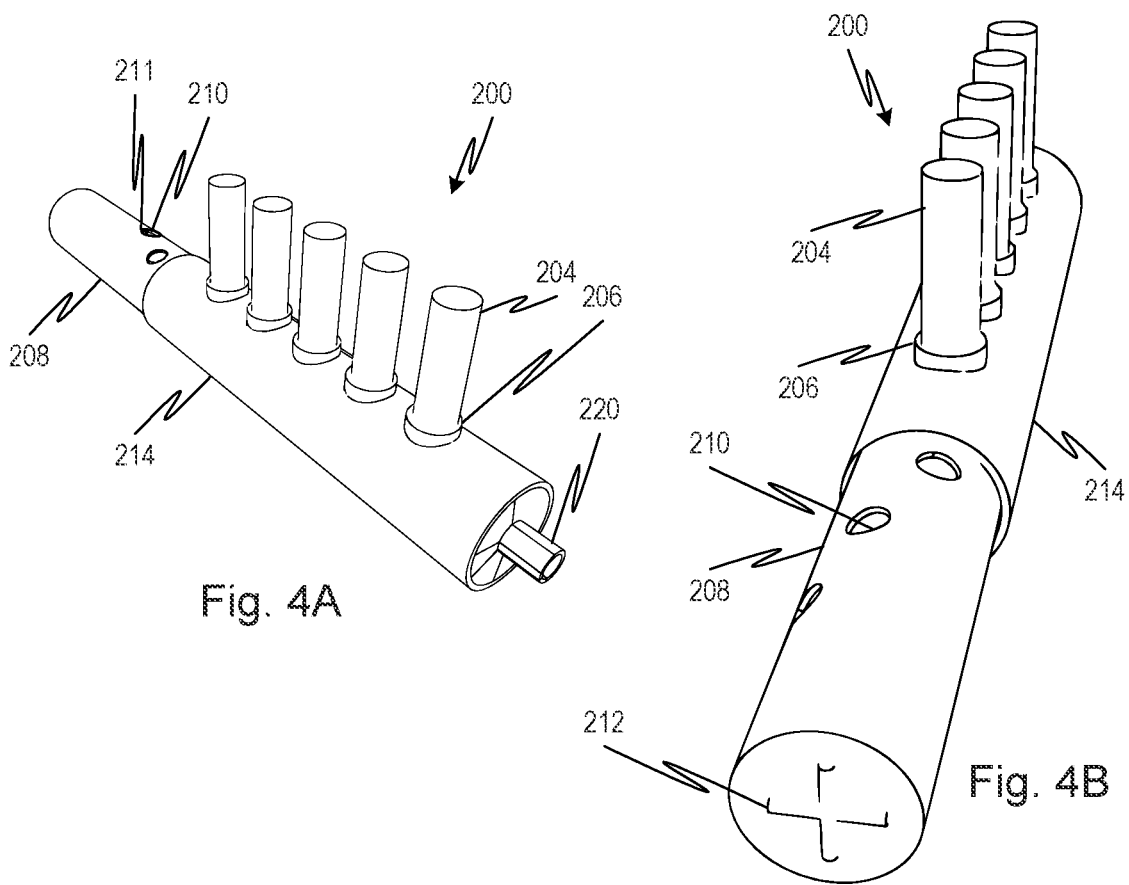

DISPOSABLE MEDICAL FLOW-REGULATING DEVICE AND SYSTEM

CROSS-REFERENCE TO RELATED APPLICATIONS

This Application is a U.S. national stage filing under 35 U.S.C. § 371 of International Application No. PCT/US2020/027246, filed Apr. 8, 2020, which claims priority to and the benefit of U.S. Provisional Patent Application No. 62/831,310 filed Apr. 9, 2019, both of which is are hereby incorporated by reference in their entireties.

FIELD OF THE INVENTION

This application is directed to a flow-regulating arrangement, particularly suited for use in an automated peritoneal dialysis system.

BACKGROUND

In an automated peritoneal dialysis system as disclosed, for example, in U.S. Pat. No. 9,861,733, incorporated herein by reference, there are a pair (at least) of fluid distribution manifolds. Each of the manifolds has an elongated configuration and two or more ports that permit fluid to flow into or out of a central chamber that runs the length of the manifold, and tubing through which various treatment fluids flow is connected to the various ports. One length of tubing extends from an outlet port of one manifold to an inlet port of the other manifold, passing through a peristaltic pump that drives fluid between the manifolds and hence throughout the various fluid-flow lines of tubing. This is illustrated, for example, in FIGS. 7A-7D and FIGS. 8A and 8D of U.S. Pat. No. 9,861,733 and the accompanying text.

Furthermore, U.S. Pat. No. 9,861,733 illustrates in FIG. 8D an arrangement in which the manifolds and peristaltic pump are housed within a clamshell-type cassette case, and the various lines of tubing leading to and from the manifolds pass across openings formed in the halves of the cassette case. As further explained in the patent, flow through the various lines of tubing may be permitted or prevented by means of a linear actuator (solenoid clamp, stepper and screw drive, pinching mechanism like a plier grip, or other kind of mechanism) that is able to access and selectively clamp each of the various lines of tubing through its respective opening.

Because the fluid distribution assembly is to be used for medical treatment, it is important that flow through the various lines of tubing be controlled (i.e., permitted or prevented) with assurance. Additionally, as a medical device that is intended to be disposed of, cost of manufacture is a consideration.

SUMMARY OF THE INVENTION

A disposable medical flow-regulating assembly includes flow-directing units, with multiple fluid-flow lines entering each of the flow-directing units. The flow-directing units are interconnected by a connecting fluid-flow line that extends between them. The fluid connecting flow line may be a pumping tube segment that is adapted to form a peristaltic pump in cooperation with a roller actuator. Each of the flow-directing units includes a rotational insert member that regulates which of multiple flow passages through the flow-directing unit is open and which are closed, based on the angular position of the insert member.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 3 is a schematic diagram illustrating the use of the porting cassette shown in FIG. 1 in the flow-porting section of an automated peritoneal dialysis system according to embodiments of the disclosed subject matter.

FIGS. 4A and 4B show respective aspects of a longitudinal cylindrical flow switch configuration according to embodiments of the disclosed subject matter.

DETAILED DESCRIPTION

A flow-regulating system 100 in accordance with the disclosed subject matter is illustrated in FIGS. 1, 2A-2C, and 3. The system utilizes a disposable porting cassette 102, which includes a pair of disc-shaped, rotary flow-directing units 104a, 104b that are housed within a clamshell-type cassette casing having side parts 106a and 106b.

Figure 1:
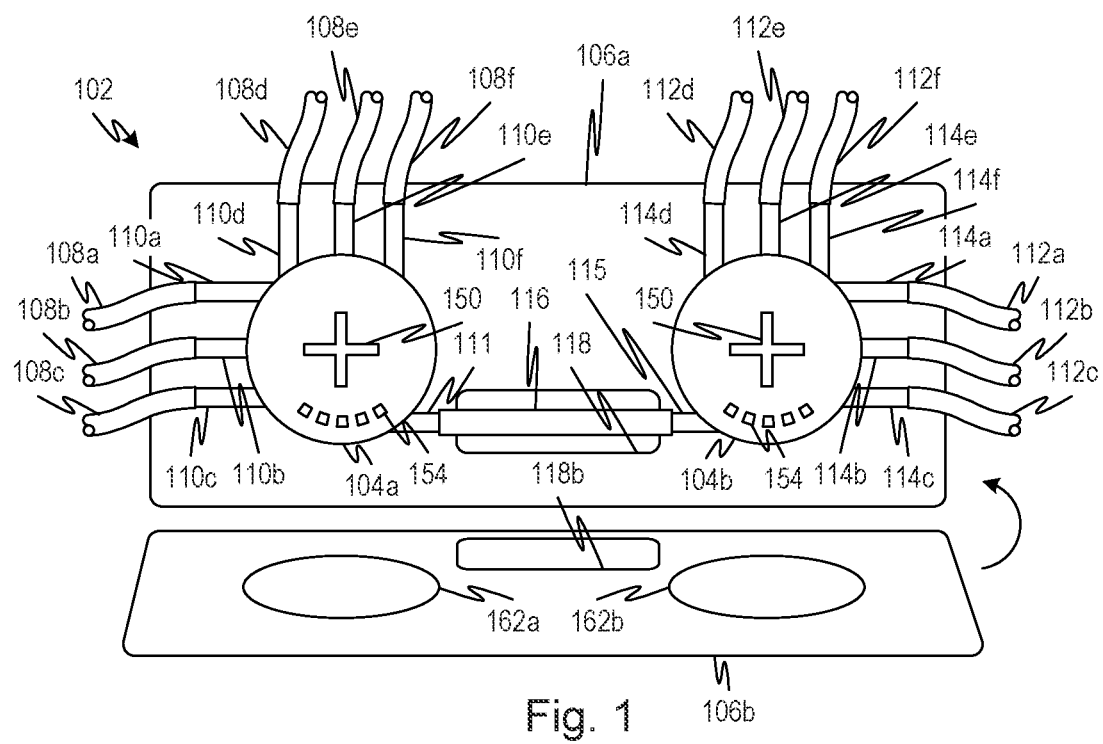
FIG. 1 is a plan view illustrating a disposable porting cassette in accordance with the disclosed subject matter according to embodiments of the disclosed subject matter.

As shown in FIG. 1, multiple incoming-fluid delivery tubes 108a-108f, made from medical-grade material, are attached to respective tube-attachment fittings 110a-110f projecting from the flow-directing unit 104a, and multiple outgoing-fluid delivery tubes 112a-112f, also made from medical-grade material, are attached to respective tube-attachment fittings 114a-114f projecting from the flow-directing unit 104b. Additionally, a pumping tube segment 116 extends between the flow-directing units 104a and 104b, attached respectively to tube-attachment fitting 111 projecting from the flow-directing unit 104a and tube-attachment fitting 115 projecting from the flow-directing unit 104b. The pumping tube segment 116 passes through a peristaltic pump 118, which can drive fluid in either direction through the pumping tube segment 116 depending on the direction of rotation of the peristaltic pump's actuator (not shown). The incoming-fluid delivery tubes 108a-108f may be attached to the tube-attachment fittings 110a-110f and outgoing-fluid delivery tubes 112a-112f may be attached to respective tube-attachment fittings 114a-114f by bonding or other suitable means known in the art.

Figure 2A:
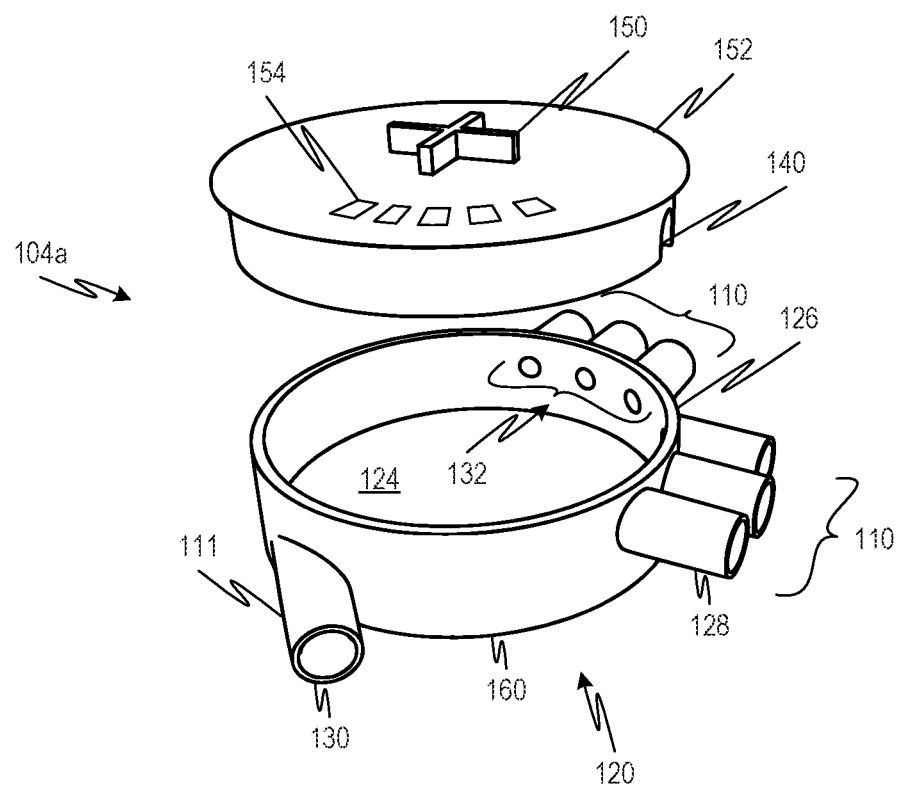
FIG. 2A is an assembly view illustrating a flow-directing unit used with the porting cassette illustrated in FIG. 1 according to embodiments of the disclosed subject matter.
Figure 2B:
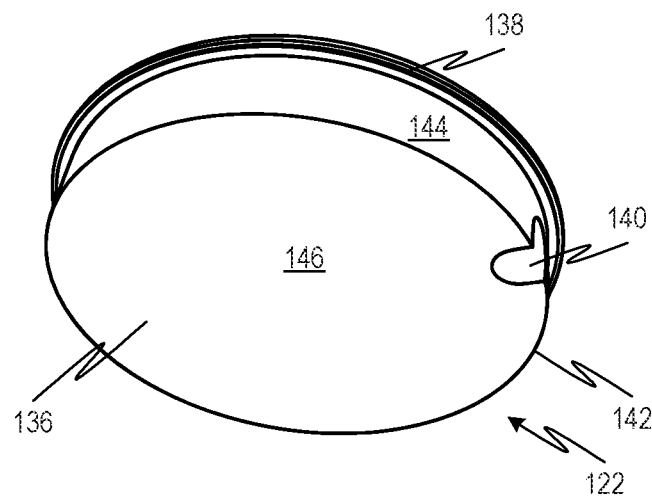
FIG. 2B is a bottom perspective view of the insert member shown in FIG. 2A according to embodiments of the disclosed subject matter.
Figure 2C:
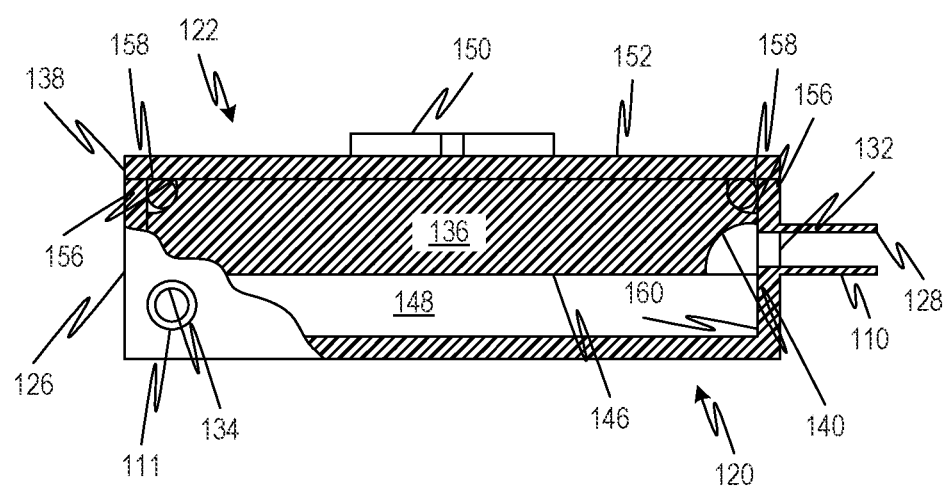
FIG. 2C is a side view, partially in section, of the flow-directing unit illustrated in FIG. 1 according to embodiments of the disclosed subject matter.

Construction of the rotary flow-directing unit 104a (e.g., with tube-attachment fittings arranged as illustrated for the flow-directing unit 104a in FIG. 1) is illustrated in FIGS. 2A-2C. The flow-directing unit 104b is similarly configured except for being a mirror image of the flow-directing unit

104a. The flow-directing unit 104a includes a generally circular, pan-shaped porting housing 120 and a disc-shaped, flow-controlling insert member 122 that fits into the porting housing 120. Both components 120 and 122 may be made from medical-grade plastic or other suitable materials.

The porting housing 120 has a circular bottom wall 124 and a ring-shaped sidewall 126, with an open top. As best shown in FIG. 2A, tube attachment fittings 110 (corresponding to the attachment fittings 110a-110f in FIG. 1) are integrally formed with and extend outwardly from the sidewall 126, as does tube attachment fitting 111. The tube attachment fittings 110, 111 are hollow and cylindrical, with open outer ends 128, 130, respectively, and are open to the interior of the porting housing 120 via apertures 132, 134, respectively. The tube attachment fittings 110, 111 may have features (not illustrated) such as hose barbs, luer locks, etc., to secure the various tubes to the tube attachment fittings 110, 111. As best illustrated in FIG. 2C, the tube attachment fittings 110 and corresponding apertures 132 are offset in the axial direction relative to the tube attachment fitting 111 and aperture 134, with the apertures 132 being located closer to the open top of the sidewall 126 and the aperture 134 being located closer to the bottom wall 124. The reason for this offset will be explained below.

The insert member 122, on the other hand, has a generally puck-shaped body 136 and a circular positioning lip or flange 138 that extends circumferentially around the upper edge of the insert member 122. As shown in FIG. 2C, the positioning flange 138 limits the extent to which the body 136 of the insert member can be inserted into the interior of the porting housing 120.

Furthermore, the insert member 122 has a notch 140 formed at the edge 142 of the insert member 122, where the peripheral surface 144 of the insert member 122 meets the bottom surface 146 of the insert member. The notch 140 forms a passageway that permits fluid to pass between the bottom surface 146 of the insert member 122 from a selected one of the tube attachment fittings 110 into a space 148 and to the attachment fitting 111. One of the attachment fittings 110 is selected depending upon the rotational position of the insert member 122.

As further illustrated in FIG. 2C, the insert member 122 is not as thick as the interior of the port housing 120 is deep. As a result, a chamber 148 is formed between the bottom surface 146 of the insert member and the bottom wall 124 of the port housing, and the apertures 134 are aligned with and opens into the chamber 148. On the other hand, the apertures 132 are vertically positioned along the sidewall 126 (i.e., in the thickness direction) such that they are blocked by the peripheral surface 144 of the insert member, unless the notch 140 is positioned in front of a given one of the apertures 132. For an aperture 132 that has the notch 140 positioned in front of it, fluid is able to flow between that aperture 132 and the chamber 148. Thus, more broadly speaking, a fluid-flow pathway will extend through the flow-directing unit 104a from the tube attachment fitting 110 and aperture 132 having the notch 140 positioned in front of it; through the notch 140 and chamber 148; and through the aperture 134 and tube attachment fitting 111. Furthermore, it will be appreciated that different apertures 132 will be opened and other apertures 132 closed depending on the rotational position of the insert member 122 within the porting housing 120.

A drive-engagement feature 150 is provided at the upper surface 152 of the insert member 122. For example, as illustrated, the drive-engagement feature 150 could be a plus sign-shaped feature that stands proud relative to the upper surface 152 of the insert member. Alternatively, the drive-engagement feature could be a slot-shaped or cross-shaped recess; a post; a divot; gear teeth extending radially from the edge of the positioning flange 138; or any other feature that can be engaged by a driving mechanism (illustrated and described below) and used to rotate the insert member 122 to a desired angular position within the porting housing 120.

Additionally, a position-indicating feature 154 may also be provided on the upper surface 152 of the insert member 122. The position-indicating feature 154 could be encoder markings that are detected by an optical sensor (illustrated and described below). Alternatively, the position-indicating feature could be indexing slots; magnets; or any other feature that can be sensed by a sensor to determine the angular position of the insert member 122.

Further still, a circumferential recess 156 is suitably formed in the peripheral surface 144 of the insert member 122, just under the positioning flange 138. A sealing member 158 such as an O-ring made from medical-grade material fits within the circumferential recess 156 and bears against the radially inner surface 160 of the sidewall 126 to seal the interior of the flow-directing unit 104. Additionally, means to secure the insert member 122 within the porting housing 120 (not illustrated) may also be provided. Such means may include clamps; a circumferential flange extending from the peripheral surface 144 of the insert member that engages with a corresponding circumferential groove formed in the radially inner surface 160 of the sidewall 126; etc.

Use of the porting cassette 102 is illustrated in FIG. 3. As shown in FIG. 1, one of the cassette side parts 106b includes a pair of apertures 162a, 162b through which the flow-directing units 104a, 104b can be accessed. The porting cassette is inserted into a receiving slot 164 within the flow-porting section of an automated peritoneal dialysis system (not illustrated), with the flow-directing units 104a, 104b aligned with and accessible to reciprocating drive members 166a, 166b through the apertures 162a, 162b. The reciprocating drive members 166a, 166b have features (e.g., end faces) that are configured to engage with the drive-engagement features 150 of the flow-distribution units 104a, 104b so that the drive members 166a, 166b can rotate the insert members 122 of the flow-distribution units 104a, 104b to various positions to open and close the various apertures 132 of the flow-distribution units. By adjusting the rotational positions of the insert members 122 of the flow-distribution units 104a, 104b, the flow of fluid through the incoming-fluid delivery tubes 108a-108f and the outgoing-fluid delivery tubes 112a-112f can be regulated.

The flow-porting section of the automated peritoneal dialysis system includes a controller 170, which receives a flow path command from the system to establish a desired combination of incoming fluid path and outgoing fluid path. The controller 170 then commands stepper motors 172a, 172b to drive the drive members 166a, 166b to commanded angular positions to achieve the desired flow path. Furthermore, position sensors 174a, 174b detect the position-indicating features 154 on the flow-distribution units 104a, 104b. In this manner, the controller 170 is provided with the necessary information to control the positions of the insert members 122 of the flow-distribution units 104a, 104b and hence to control the overall fluid-flow pathway.

Given the relatively compact design of the fluid-distribution units, they can be fabricated relatively inexpensively. This is beneficial for medical components that are to be disposed of. Additionally, the design reduces complexity of the overall peritoneal dialysis system in that the settings for just two components—namely, the angular positions of the insert members of the two flow-distribution units—needs to be regulated instead of the actuation states of clamping devices on each of the various fluid-flow lines. Further still, the design affords high assurance that flow will be prevented or allowed through the various lines.

Another configuration of a flow-directing unit 200 is illustrated in FIGS. 4A and 4B. Each flow-directing unit 200 has a flow barrel 214 with ports 206 connecting fluid circuit elements, one of which is indicated at 204, to form a manifold. Each flow-directing unit 200 has a selector drum 208 that engages with a selector drive (not shown but similar to that shown in FIG. 3) by means of a drive-engagement feature 212. Ports 206 align with the ports 210 to connect a selected port 206 to a common port 220. The flow directing unit 200 is used in symmetrical pairs as are flow-directing units 104a and 104b. Each flow-directing unit 200 common port 220 connects to a pumping tube segment (not shown but arranged similarly to the arrangement shown in FIG. 1). Thus each of two of the flow-directing units 200 would have its port 220 facing the other and connected to that other port 220 by the pumping tube segment (again, not shown). The selector drum 208 is shown extended out of the flow barrel 214 to reveal the ports 210 that would otherwise be hidden, but it will be understood that the selector drum is positioned inside the barrel 214 during use. Each port 210 may have an O-ring 211 to seal it against the inner wall of the barrel 214 to form a seal with a respective one of the ports 206. It will be evident from the drawing and the above description that independent pump inlet and pump outlet channels of a fluid circuit may be selected using the above configuration. Although not shown, indicia can be provided on the ends of the selector drum 208 to indicate the angular position of the selector drum.

According to embodiments, the disclosed subject matter includes a disposable medical flow-regulating device having a pair of cylindrical flow-directing units, with each of the flow-directing units having a housing with tube attachment fittings directed approximately radially away from an axis of the flow-directing unit and a transfer fitting. A pumping tube segment extends from the transfer fitting on one of the flow-directing units to the transfer fitting on the other of the flow-directing units to establish a fluid flow path between the two flow-directing units. Each of the flow-directing units having a disc-shaped, rotary insert member rotates within a chamber to select one of the tube attachment fittings at a given angular position thereof to connect with respective one of the transfer fittings whereby a selectable channel from a first flow-directing unit tube attachment fitting to a second flow-directing unit tube attachment fitting is defined. Tubing elements from a fluid circuit are connected the tube attachment fittings of each of the flow-directing units such that selectable flow paths in the fluid circuit may be defined by rotating the rotary insert members.

In further variations of the embodiments, each of the rotary insert members seals to a respective housing using an O-ring. In further variations of the embodiments, a flow chamber is defined between each rotary insert member and a respective one of the housings. In further variations of the embodiments, there may be included a respective rotary actuator that engages with a respective one of the rotary insert members. In further variations of the embodiments, the pair of cylindrical flow-directing units and the pumping tube segment are partially enclosed in a support member to form a cartridge enclosure. In further variations of the embodiments, the support has openings to provide access to the rotary insert members and the pumping tube segment.

According to further embodiments, the disclosed subject matter includes a selector valve with first and second flow switches, each having a cylindrical chamber with a rotary element that selectively interconnects a common port with a selected one of a plurality of individual ports. The cylindrical chamber and rotary element forming a fluid passage defined by a hollow space between them. The common port of each of said pair being connected to a respective end of a pumping tube segment. A rotary actuator is provided for each of said rotary elements and a controller configured to rotate the rotary elements independently to define selected interconnections in a fluid circuit connected to the plurality of individual ports.

In variations thereof, the embodiments include ones in which each of the rotary elements seals to a respective one of the cylindrical chambers by means of an O-ring.

In variations thereof, the embodiments include ones in which the pair of flow switches and the pumping tube segment are partially enclosed in a support member to form a cartridge enclosure. In variations thereof, the embodiments include ones in which the support has openings to provide access to the rotary elements and the pumping tube segment.

We claim:

1. A disposable medical flow-regulating device, comprising:
   a first cylindrical flow-director and a second cylindrical flow-director, each of the first and second cylindrical flow-directors including
      a pan-shaped hollow housing having a circular bottom wall and a side wall around an outer perimeter of the circular bottom wall, with a plurality of tube attachment fittings extending out of an outer surface of the side wall, each of the tube attachment fittings being in fluid communication with an interior cavity of the pan-shaped hollow housing,
      a first tube attachment fitting of the plurality of tube attachment fittings having a position closer to the circular bottom wall than all others of the plurality of the tube attachment fittings, and
      a rotary insert that is configured to rotate within the interior cavity of the pan-shaped hollow housing, the rotary insert having a peripheral wall with a height that is less than a height of the side wall of the pan-shaped hollow housing, such that the peripheral wall occludes the others of the plurality of the tube attachment fittings but does not occlude the first tube attachment fitting when the rotary insert is fully inserted into the pan-shaped hollow housing, and the rotary insert having a notch in the peripheral wall that allows a selected one of the others of the plurality of the tube attachment fittings to fluidly communicate with the first tube attachment fitting when the notch is positioned adjacent to the selected one of the others of the plurality of the tube attachment fittings;
   a pumping tube segment compatible with a peristaltic pump, the pumping tube segment extending from the first tube attachment fitting of the first cylindrical flow-director to a first tube attachment fitting of the second cylindrical flow-director to establish a fluid flow path between the first and the second cylindrical flow-directors;
   fluid delivery tubes connected to the others of the plurality of the tube attachment fittings of each of the first and second cylindrical flow-directors such that selectable flow paths between the fluid delivery tubes are defined by rotating a respective rotary insert.

2. The device of claim 1, wherein each rotary insert seals to a respective pan-shaped hollow housing using an O-ring.

3. The device of claim 1, wherein a flow chamber is defined between each rotary insert and the circular bottom wall of a respective pan-shaped hollow housing.

4. The device of claim 1, further comprising a drive-engagement feature on a top surface of each rotary insert that is configured to engage with a driving mechanism.

5. The device of claim 1, wherein each of the first and second cylindrical flow-directors and the pumping tube segment are partially enclosed in a support frame to form a cartridge enclosure.

6. The device of claim 5, wherein the support frame has openings to provide access to the rotary inserts and the pumping tube segment.

7. The device of claim 1, wherein the rotary inserts are disc shaped.

* * * * *